(12) United States Patent
Martis et al.

(10) Patent No.: US 6,306,836 B1
(45) Date of Patent: Oct. 23, 2001

(54) PERITONEAL DIALYSIS SOLUTIONS CONTAINING MALTODEXTRINS AND AMINO ACIDS

(75) Inventors: Leo Martis, Long Grove; Ron Burke, Arlington Heights; Ty Shockley, Highland Park; Lee W. Henderson, Lake Forest, all of IL (US); Bernadette Faller, Colmar (FR)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/184,813

(22) Filed: Jan. 21, 1994

(51) Int. Cl.$^7$ ..................................................... A61K 31/70
(52) U.S. Cl. .................. 514/58; 514/54; 514/60
(58) Field of Search .................. 514/54, 58, 60; 210/647, 297

(56) References Cited

FOREIGN PATENT DOCUMENTS

| 0 076 355 A3 | 4/1983 | (EP) . |
| 0 153 164 A2 | 8/1985 | (EP) . |
| 0 207 676 A3 | 1/1987 | (EP) . |

*Primary Examiner*—Elli Peselev
(74) *Attorney, Agent, or Firm*—Charles R. Mattenson; Paula J. Kelly; Robert M. Barrett

(57) ABSTRACT

A peritoneal dialysis solution comprising as osmotic agents approximately 2.0 to about 6.0% (w/v) maltodextrins and approximately 0.25 to about 2.0% (w/v) amino acids. The peritoneal dialysis solution will also include other components such as sodium, chloride, lactate, bicarbonate, calcium, and magnesium.

22 Claims, 5 Drawing Sheets

PERITONEAL DIALYSIS SOLUTIONS CONTAINING MALTODEXTRINS AND AMINO ACIDS

BACKGROUND OF THE INVENTION

The present invention relates generally to peritoneal dialysis. More specifically, the present invention relates to peritoneal dialysis solutions.

It is known to use dialysis to support a patient whose renal function has decreased to the point where the kidneys no longer sufficiently function. Two principal methods of dialysis are utilized: hemodialysis; and peritoneal dialysis. Hemodialysis utilizes an artificial kidney dialysis machine through which the patient's blood is passed. A membrane in the machine acts as an artificial kidney and cleanses the blood. Hemodialysis is an extracorporeal treatment that requires special machinery. Therefore, there are certain inherent disadvantages with hemodialysis.

Peritoneal dialysis was developed to overcome some of the disadvantages associated with hemodialysis. In peritoneal dialysis, a patient's own peritoneum is used as a semi-permeable membrane. The peritoneum is capable of acting as a natural semi-permeable membrane due to the large number of blood vessels and capillaries present in this membranous lining of the body cavity.

In peritoneal dialysis, a dialysis solution is introduced into the peritoneal cavity utilizing a catheter. After a sufficient period of time, an exchange of solutes between the dialysate and the blood is achieved. By providing a suitable osmotic gradient from blood to dialysate, fluid removal is achieved permitting water outflow from the blood. This allows the proper acid-base, electrolyte and fluid balance to be returned to the blood and the dialysis solution is simply drained from the body cavity through the catheter.

There are many advantages to peritoneal dialysis. However, one of the difficulties that has been encountered is providing a dialysate that includes a suitable osmotic agent. What is required is that a sufficient osmotic gradient is achieved. To achieve the osmotic gradient, an osmotic agent is used. The osmotic agent maintains the osmotic gradient required to cause transport of water and toxic substances across the peritoneum into the dialysis solution.

In order to be suitable, the osmotic agent needs to achieve at least a couple of criteria. First, it needs to be non-toxic and substantially biologically inert. However, the agent should be metabolizable. The agent should not rapidly cross the peritoneum membrane into the blood. By achieving both these criteria, one is able to allow maintenance of the maximum ultrafiltration gradient, and also prevent toxicity or accumulation of unwanted substances in the blood.

It is believed that no currently used substances currently satisfy the criteria for an osmotic agent in a dialysis solution. The most widely used osmotic agent today is dextrose. Dextrose is fairly safe and is readily metabolizable if it enters the blood.

But, one of the problems encountered with dextrose is that it is rapidly taken up by the blood from the dialysate. Because dextrose crosses the peritoneum so rapidly, the osmotic gradient is dissipated within two to three hours of infusion. This can cause reversal of the direction of ultrafiltration, causing water to be reabsorbed from the dialysate toward the end of the time allowed for the exchange.

A further concern with respect to dextrose is that because it is taken up so rapidly by the blood, it can represent a large proportion of the patient's energy intake. In non-diabetic patients, this may not be significant. However, this can represent a severe metabolic burden to a patient whose glucose tolerance is already impaired. Dextrose can also cause problems with respect to patients having hyperglycemia or who are obese.

A further problem experienced with dextrose is with respect to the preparation of a dialysis solution. Dialysis solutions, similar to other medical products and solutions, are typically sterilized by heating. Unfortunately, heat sterilization of dextrose at physiological pHs will cause dextrose to caramelize. To compensate for this problem, it is known to adjust the pH of the dialysate to within the range of 5 to 5.5—at this low pH, dextrose caramelization will be minimal when heated. However, it is believed that this low pH may be responsible for the pain some patients experience on the in-flow of dialysis solution. Additionally, the low pH of the solution may cause other problems, e.g., may effect peritoneal host defense.

To address some of the above concerns, a number of substances have been proposed as alternatives to dextrose. It is believed that none of the proposed materials currently available have proven to be an adequate substitute for dextrose.

Dextrans, polyanions, and glucose polymers have been suggested as replacements for dextrose. Because of their high molecular weight, it is believed that their diffusion across the peritoneum and into the blood should be minimized. But, the low osmotic activity per unit mass of these materials dictates the need for larger concentrations (w/v) of these materials in the dialysis fluids in order for them to be effective. Additionally, systemic absorption of these materials, mainly through the lymphatics, along with slow metabolism, raises serious concerns about the long term safety of these agents.

Small molecular weight substances have also been explored. These substances include glycerol, sorbitol, xylitol, and fructose. However, these substances are believed to raise a number of safety concerns while offering no substantial advantage over dextrose.

An attractive substitute for dextrose appears to be amino acids. Short term studies have indicated that amino acids are well tolerated. But, because of their low molecular weights, they are transported quite rapidly through the peritoneum resulting in a rapid loss of osmotic gradient. Additionally, the rapid uptake of amino acids leads to a considerable nitrogen burden and limits the use of amino acids to one to two exchanges per day.

Recently, polypeptides have been explored as a potential class of osmotic agents. It is believed that polypeptides will have a slow transport across the peritoneum and therefore maintain a prolonged osmotic gradient between the dialysate and blood. U.S. Pat. No. 4,906,616 to Gilchrist et al and European Patent No. 0218900 to Klein set forth polypeptides as the osmotic agent in the peritoneal dialysis solution. Each of these patents discusses the substitution of polypeptides for dextrose. As disclosed, polypeptides are the only osmotic agents utilized in these formulations.

It is believed that the polypeptide solutions proposed by Klein and Gilchrist et al have very limited clinical use. Although larger in size, like amino acids, these polypeptide compositions are absorbed from the peritoneum quite rapidly. This leads to uremic symptoms. In addition, these materials containing polypeptides have the potential of producing allergic reactions. This is due to the size of polypeptides that are used.

Glucose polymers have also been explored in peritoneal dialysis solutions. U.S. Pat. No. 4,761,237 discloses the use of glucose polymers in a dialysis solution. EP 0 076 355 discloses a dialysis solution comprising the conventional electrolyte combination of sodium, calcium, magnesium, chloride, lactate, and sodium hydroxide with the alleged improvement comprising the use of a glucose polymer as the osmotic agent. EP 0 153 164 discloses a peritoneal dialysis solution having an osmotic agent that is a glucose polymer mixture. U.S. Pat. No. 4,886,789 is believed to relate to EP 0 153 164.

It is believed that the disclosed solutions do not overcome all of the issues set forth above.

There is therefore a need for an improved peritoneal dialysis solution.

SUMMARY OF THE INVENTION

The present invention provides an improved dialysis solution. The improved dialysis solution provides for the use of a mixture of amino acids and maltodextrins as the osmotic agent in a peritoneal dialysis solution.

To this end, the present invention provides, in an embodiment, a peritoneal dialysis solution comprising as osmotic agents approximately 2 to about 6% (w/v) maltodextrins and approximately 0.25 to 2% (w/v) of a mixture of essential and non-essential amino acids.

In an embodiment, the amino acids comprise both essential and non-essential amino acids.

In an embodiment, the solution includes: 120 to about 140 (mEq/L) sodium; 70 to about 110 (mEq/L) chloride; 0 to about 45.00 (mEq/L) of lactate; 0 to about 45.00 (mEq/L) of bicarbonate; 0 to about 4.00 (mEq/L) of calcium; and 0 to about 4.00 (mEq/L) of magnesium.

In an embodiment, the maltodextrins are derived from the hydrolysis of starch and have the following compositon:

| Weight Average Mol. Wt. (Mw) | 10,000–16,000 daltons |
|---|---|
| Number Average Mol. Wt. (Mn) | 4,000–8,000 daltons |
| Polydispersity | 1.0–4.0 |
| Fraction > 100,000 daltons | NMT 1.0% |
| Mono, Di, Trisaccharides | NMT 5.0% |
| Distribution | normal |
| Alpha (1–4) | NLT 90% |
| Aluminum (10% solution) | <10 ppb |
| Aqueous Solubility | NLT 10% (w/v) |
| pH (10% solution) | 5.0–7.0 |
| Heavy Metals | <5 ppm |
| DP (Degree of polymerization) | |
| greater than 20 | ≧75% |
| DP greater than 50 | ≧50% |
| DP greater than 100 | ≧25% |

In an embodiment, the amino acids comprise:

| Amino Acid | Conc. (mg %) |
|---|---|
| Leucine | 74–112 |
| Valine | 100–151 |
| Threonine | 47–71 |
| Isoleucine | 61–92 |
| Lysine.HCl | 55–83 |
| Histidine | 52–78 |
| Methionine | 32–48 |
| Phenylalanine | 42–62 |

-continued

| Amino Acid | Conc. (mg %) |
|---|---|
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83 |

In an embodiment, the amino acids are chosen so as to have the following ratios:

Phenylalanine/Tyrosine 1.3–3.0

Essential/Total Amino Acids 0.4–0.7

In an embodiment, the maltodextrins and amino acids comprise the only osmotic agents in the solution.

In another embodiment, a peritoneal dialysis solution is provided that comprises:

| Maltodextrins (% w/v) | 2.0–6.0 |
|---|---|
| Amino Acids (% w/v) | 0.25–2.0 |
| Sodium (mEq/L) | 120–140 |
| Chloride (mEq/L) | 70–110 |
| Lactate (mEq/L) | 0.0–45.0 |
| Bicarbonate (mEq/L) | 0.0–45.0 |
| Calcium (mEq/L) | 0.0–4.0 |
| Magnesium (mEq/L) | 0.0–4.0 |
| pH | 6.0–7.4 |

In an embodiment, a method for providing an osmotic agent for a peritoneal dialysis solution is provided comprising the steps of selecting as the osmotic agent two compositions, one having a weight average molecular weight equal to or greater than 10,000 daltons and comprising approximately 2.0 to about 6.0% (w/v) of the composition and a second composition having a molecular weight equal to or less than 300 daltons and comprising approximately 0.25 to about 2.0% w/v of the composition.

In an embodiment of the method, the osmotic agent includes maltodextrin and amino acids.

In another embodiment, a two part peritoneal dialysis solution designed to be mixed prior to infusion into a patient is provided comprising: a first part housed in a first structure including approximately 2.0 to about 6.0% (w/v) maltodextrins and a pH of approximately 4.0 to about 5.5; a second part housed in a second structure including amino acids; and including in either the first or the second structure a sufficient amount of the following ingredients so that when the first part and second part are mixed the following is provided: 120 to about 140 (mEq/L) sodium; 70.0 to about 110.00 (mEq/L) chloride; 0.0 to about 45.0 (mEq/L) lactate; 0.0 to about 45.0 (mEq/L) bicarbonate; 0.0 to about 4.0 mEq/L) calcium; and 0.0 to about 4.0 (mEq/L) magnesium.

In a preferred embodiment, the sum of lactate plus bicarbonate is within the range of 20 to about 45 (mEq/L)

An advantage of the present invention is that it provides an improved peritoneal dialysis solution.

Still further, an advantage of the present invention is that it provides an improved osmotic agent for use in a peritoneal dialysis solution.

A further advantage of the present invention is that it provides a dialysis solution that allows for sustained ultrafiltration over long dwells.

Moreover, an advantage of the present invention is that it provides a combination of large and small molecular weight solutes.

An advantage of the present invention is that it provides the option of increasing infusion volume to provide improved efficiency.

Another advantage of the present invention is that it provides for the combination of osmotic agents to provide improved safety.

Furthermore, an advantage of the present invention is that it provides a balanced peritoneal supplementation of calorie and nitrogen source to improve nutritional status.

Further, an advantage of the present invention is that it provides a solution having a physiological pH to help reduce the pain on infusion experienced by a number of peritoneal dialysis patients.

Moreover, an advantage of the present invention is that it provides reduced osmolalities along with a physiological pH to restore peritoneal cell functions.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
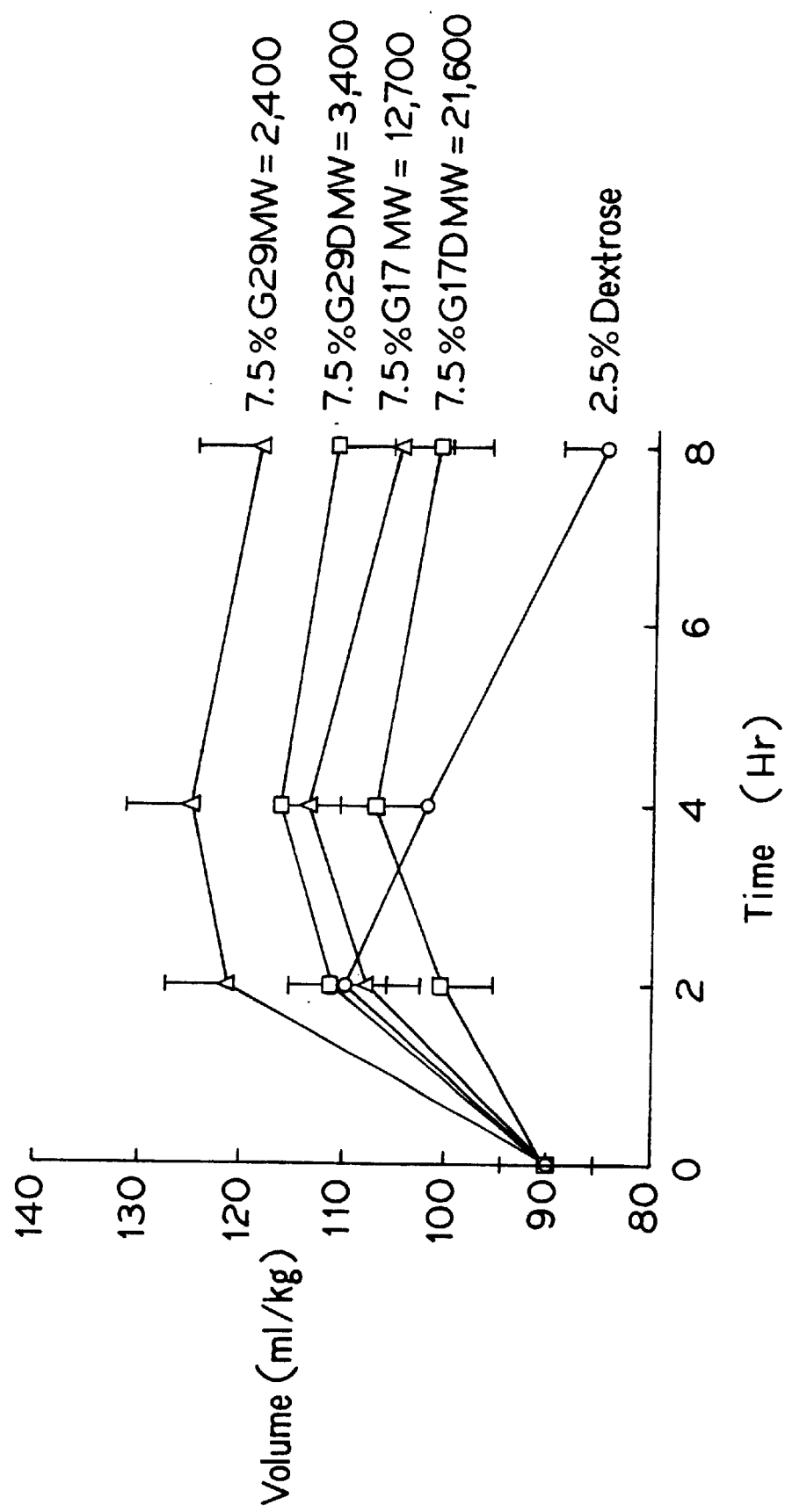
FIG. 1 illustrates graphically peritoneal volume profiles over time of solutions pursuant to the experiment set forth below.

The present invention provides improved peritoneal dialysis solutions that preferably contain maltodextrins and amino acids as an osmotic agent. Preferably, the dialysis solution contains a mixture of well-defined amino acids and maltodextrins for use as the osmotic agent in peritoneal dialysis solutions.

As set forth in detail below, by using amino acids and maltodextrins in a peritoneal dialysis solution as the osmotic agent, the disadvantages of typical osmotic agents can be overcome. The maltodextrins and amino acids provide an osmotic agent that provides a combination of low and high molecular weight solutes. Preferably, approximately 0.25% to about 2% (w/v) of a mixture of essential and non-essential amino acids is utilized with approximately 2 to about 6 (w/v) maltodextrins as the osmotic agent.

Preferably, the maltodextrins utilized are derived from the hydrolysis of starch. Preferably, the maltodextrins have the following composition:

| | |
|---|---|
| Weight Average Mol. Wt. (Mw) | 10,000–16,000 |
| Number Average Mol. Wt. (Mn) | 4,000–8,000 |
| Polydispersity | 1.0–4.0 |
| Fraction > 100,000 daltons | NMT 1.0% |
| Mono, Di, Trisaccharides | NMT 5.0% |
| Distribution | normal |
| Alpha (1–4) | NLT 90% |
| Aluminum (10% solution) | <10 ppb |
| Aqueous Solubility | NLT 10% (w/v) |
| pH (10% solution) | 5.0–7.0 |
| Heavy Metals | <5 ppm |
| DP (Degree of polymerization) | |
| greater than 20 | ≧75% |
| DP greater than 40 | ≧50% |
| DP greater than 80 | ≧25% |

In addition to maltodextrins, preferably, the solution contains a mixture of essential and nonessential amino acids having the following composition:

| Amino Acid | Conc. (mg %) |
|---|---|
| Leucine | 74–112 |
| Valine | 100–151 |
| Threonine | 47–71 |
| Isoleucine | 61–92 |
| Lysine. HCl | 55–83 |
| Histidine | 52–78 |
| Methionine | 32–48 |
| Phenylalanine | 42–62 |
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83 |

Preferred Ratios
  Phenylalanine/Tyrosine 1.3–3.0
  Essential/Total Amino Acids 0.4–0.7

Although preferably maltodextrins and amino acids are used as the osmotic agent, other high molecular weight and low molecular weight compositions can be used in combination. It is believed that the high molecular weight composition should have a weight average molecular weight greater than or equal to 10,000 daltons. The low molecular weight composition should have a molecular weight less than or equal to 300 daltons. Preferably, the compositions have molecular weights within the following ranges, respectively: approximately 10,000 to about 16,000 daltons; and approximately 100 to about 300 daltons.

By way of example, and not limitation, an example of a solution of the present invention is as follows:

| | |
|---|---|
| Maltodextrins (% w/v) | 2.0–6.0 |
| Amino Acids (% w/v) | 0.25–2.0 |
| Sodium (mEq/L) | 120–140 |
| Chloride (mEq/L) | 70–110 |
| Lactate (mEq/L) | 0.0–45.0 |
| Bicarbonate (mEq/L) | 0.0–45.0 |
| Calcium (mEq/L) | 0.0–4.0 |
| Magnesium (mEq/L) | 0.0–4.0 |
| pH | 6.0–7.4 |

In the example above, the components that are not compatible with each other can be separated during sterilization and mixed together prior to infusion. By way of example, and not limitation, the composition can be contained in separate chambers or containers, as follows:

|  | Chamber 1 | Chamber 2 |
|---|---|---|
| Maltodextrin (% w/v) | 2–6.0 |  |
| Amino acids (% w/v) | 0.0 | .25–2.0 |
| Sodium (mEq/L) | 0–300 | 0–300 |
| Chloride (mEq/L) | 0–250 | 0–250 |
| Lactate (mEq/L) | 0–100 | 0–100 |
| Bicarbonate (mEq/L) | 0–100 | 0–100 |
| Calcium (mEq/L) | 0–10 | 0–10 |
| Magnesium (mEq/L) | 0–5.0 | 0–5.0 |
| pH | 4.0–5.5 | 6.0–7.5 |

Preferably, only maltodextrin is contained in chamber 1. In an embodiment, lactate is contained in chamber 1 along with maltodextrin.

The contents of the two chambers are mixed prior to infusion into the peritoneal cavity of the patient.

Figure 5:
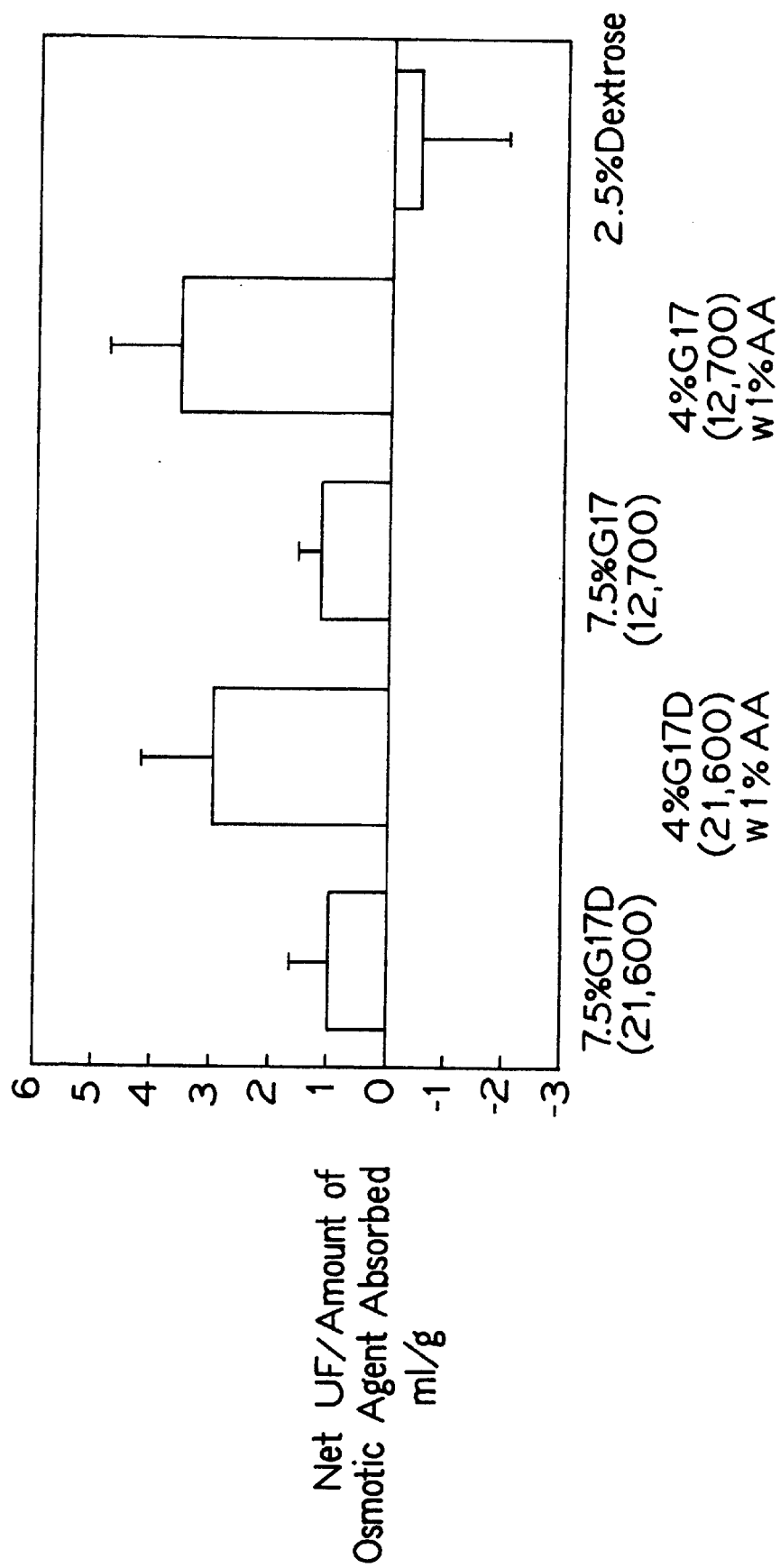
FIG. 5 illustrates graphically solution performance pursuant to the experiment set forth below.

By way of example, and not limitation, an animal model of peritoneal dialysis is set forth below. Through the animal model, it was observed that solutions containing a combination of large solutes (mw 10,000–16,000 daltons) and small solutes (molecular weight 100 to 300 daltons), are ideal for fluid and solute transport for patients on peritoneal dialysis. The experiment also suggests that a solution containing the combined osmotic agents is more effective than a solution containing either of the osmotic agents alone. When maltodextrin of the composition defined by the present invention was used as the large solute along With amino acids, in proportions outlined above, unexpected benefit in dialysis efficiency as determined by ultrafiltration per gram of osmotic agent absorbed was observed over long dwells. See FIG. 5.

EXAMPLE NO. 1

Introduction

Maltodextrins of varying molecular weight averages were investigated as alternate osmotic agents to dextrose in peritoneal dialysis solutions administered to normal rats. Additional experiments using maltodextrins/amino acids in combination were also conducted.

Material Preparation

Maltodextrin powders, varying in the degree of enzymatic hydrolysis, were used in these experiments.

5% (w/v) solutions were prepared and assayed for weight, osmolality, and pH as shown below:

| Sample ID | Weight Average Mw | Osmolality (mosm/kg) | pH |
|---|---|---|---|
| G6 | 38000 | 17 | 5.3 |
| G17 | 12700 | 38 | 5.1 |
| G29 | 2400 | 65 | 5.2 |
| G40 | 2000 | 103 | 5.3 |
| G17D | 21600 | 30 | 5.1 |
| G29D | 3400 | 44 | 5.2 |

Individual amino acids were prepared on a weight percent basis as follows: Leu 8.45%; Val 12.27%; Thr 5.36%; Ile 7.00%; Lys 5.45%; His 5.91%; Met 3.64%; Phe 4.73%; Trp 2.27%; Ala 7.73%; Pro 4.91%; Arg 6.82%; Gly 4.18%; Ser 5.45%; Tyr 2.73%; Asp 6.55%; and Glu 6.55%.

The maltodextrins were formulated alone or in combination with amino acids as summarized in Table 1. Following dissolution of all solution components, solutions were sterile filled through a 0.22 μm filter unit into Viaflex® bags. $^{14}$C dextran in saline was injected into each solution bag (1 μCi/30 ml) as a dilution marker for measuring peritoneal volume.

Solutions were analyzed for pH, osmolality, sodium, and chloride.

TABLE 1

Composition of Maltodextrin Dialysate Solutions

|  | 7.5% G17D | 7.5% G17 | 7.5% G29D |
|---|---|---|---|
| Component |  |  |  |
| Maltodextrin (g/L) | 75 | 75 | 75 |
| Amino Acid Blend (g/L) |  |  |  |
| Target |  |  |  |
| Sodium (mEq/L) | 132 | 132 | 132 |
| Chloride (mEq/L) | 96 | 96 | 96 |
| Lactate (mEq/L) | 40 | 40 | 40 |
| Calcium (mEq/L) | 3.5 | 3.5 | 3.5 |
| Magnesium (mEq/L) | 0.5 | 0.5 | 0.5 |
| Electrolyte Total (mEq/L) | 272 | 272 | 272 |
| Assayed components |  |  |  |
| Osmolality (mOsm/kg) | 302 | 322 | 352 |
| pH | 5.1 | 5.1 | 5.1 |
| Sodium (mEq/L) | 126 | 126 | 126 |
| Chloride (mEq/L) | 96 | 96 | 96 |
| Maltodextrin GPC |  |  |  |
| Average Moleoular Wt. | 21,600 | 12,700 | 3,400 |

|  | 7.5% G29 | 3% G17D/ 0.75% AAs | 3% G17/ 0.75% AAs |
|---|---|---|---|
| Component |  |  |  |
| Maltodextrin (g/L) | 75 | 30 | 30 |
| Amino Acid Blend (g/L) |  | 7.5 | 7.5 |
| Target |  |  |  |
| Sodium (mEq/L) | 132 | 132 | 132 |
| Chloride (mEq/L) | 06 | 96 | 96 |
| Lactate (mEq/L) | 40 | 40 | 40 |
| Calcium (mEq/L) | 3.5 | 3.5 | 3.5 |
| Magnesium (mEq/L) | 0.5 | 0.5 | 0.5 |
| Electrolyte Total (mEq/L) | 272 | 272 | 272 |
| Assayed components |  |  |  |
| Osmolality (mOsm/kg) | 374 | 327 | 333 |
| pH | 5.1 | 7.0 | 7.0 |
| Sodium (mEq/L) | 126 | 123 | 126 |
| Chloride (mEq/L) | 96 | 93 | 96 |
| Maltodextrin GPC |  |  |  |
| Average Molecular Wt. | 2,400 | 21,600 | 12,700 |

|  | 3% G29D/ 0.75% AAs | 1% AA | 4% G17D/1% AAs | 4% G17/ 1% AAs |
|---|---|---|---|---|
| Component |  |  |  |  |
| Maltodextrin (g/L) | 30 |  | 40 | 40 |
| Amino Acid Blend (g/L) | 7.5 | 10 | 10 | 10 |
| Target |  |  |  |  |
| Sodium (mEq/L) | 132 | 132 | 132 | 132 |
| Chloride (mEq/L) | 96 | 96 | 96 | 96 |
| Lactate (mEq/L) | 40 | 40 | 40 | 40 |
| Calcium (mEq/L) | 3.5 | 3.5 | 3.5 | 3.5 |
| Magnesium (mEq/L) | 0.5 | 0.5 | 0.5 | 0.5 |

TABLE 1-continued

Composition of Maltodextrin Dialysate Solutions

| (mEq/L) | | | | |
|---|---|---|---|---|
| Electrolyte Total (mEq/L) | 272 | 272 | 272 | 272 |
| Assayed components | | | | |
| Osmolality (mOsm/kg) | 342 | 335 | 360 | 370 |
| pH | 7.0 | 7.0 | 7.0 | 7.0 |
| Sodium (mEq/L) | 130 | 132 | 131 | 132 |
| Chloride (mEq/L) | 100 | 99 | 99 | 100 |
| Maltodextrin GPC | | | | |
| Average Molecular Wt. | 3,400 | | 21,600 | 12,700 |

Experimental Procedure

7.5% Maltodextrins Administered Alone

Male Sprague-Dawley rats (Harlan Sprague Dawley Inc., Indianapolis, Indiana) weighing 300–370 grams were administered 7.5% (w/v) maltodextrin solutions (n=6/group) during the course of two treatment days. Prior to solution injection, a 1.5 ml baseline blood sample was collected via the tail vein. Plasma was separated by centrifugation @ 12,000×g for 10 minutes and stored frozen.

On a given treatment day, each rat was weighed, anesthetized by Metafane inhalation, the abdominal area shaved, and dialysate solution (90 ml/kg) injected intraperitoneally using a 23 needle. Dialysate solutions were warmed to room temperature prior to injection. The dialysis solution (25–35 ml) contained approximately 1 $\mu$Ci $^{14}$C Dextran as a dilution marker for measuring peritoneal volume.

Rats were allowed to recover and were permitted free access to water. Dialysate samples (0.2 ml) were collected at 2 and 4 hours during the dwell period and frozen. A 2 hour blood sample was also collected for dialysate to plasma ratios (D/P) of urea and creatinine determinations.

At the end of the 8 hr dwell period, a 2 ml blood sample was collected via the tail artery, and plasma was separated and frozen. Rats were euthanized by tail vein injection of T-61 solution. The abdominal cavity was immediately opened by midline incision, dialysate collected, and volume recorded by weight. A 5 ml dialysate sample was stored frozen for further analyses.

3% Maltodextrins/0.75% Amino Acids

The dialysis procedure, as previously described was performed using Sprague-Dawley rats weighing 270–400 grams. Rats were administered either 3% maltodextrin/0.75% amino acid solutions or 4.25% Dextrose Dianeal solution (n=6/group) during the course of two treatment days.

4% Maltodextrins/1% Amino Acids

The dialysis procedure, as previously described was performed using Sprague-Dawley rats weighing 350–380 grams. Rats were administered either 4% maltodextrin/1% amino acid solutions or 1% amino acids alone (n=6/group) during the course of one treatment day.

Sample Analyses

Osmolality

All dialysate solutions were assayed for osmolality by freezing point depression. (Osmometer Advanced Instruments Model (3MO)

$^{14}$C Dextran

All dialysate samples were assayed for radiolabelled dextran. 0.1 or 0.05 ml of dialysate sample was added to 1 ml of water in 7 ml glass scintillation vials. 3 ml of Ready Gel Scintillation cocktail (Beckman) was added and the vials shaken until gelled. Samples were counted on Beckman Scintillation Counter Model LS 5000 TD.

Maltodextrins

Fresh and spent dialysate samples were assayed for maltodextrin content by enzymatic hydrolysis to free glucose. 50 $\mu$L of dialysate sample was incubated with 950 $\mu$L of 0.6 mg/ml amyloglucosidase in 0.01M sodium acetate for 1 hour at 55° C. Hydrolyzed solutions were then assayed for glucose by the following method: Glucose phosphorylation is catalyzed by hexokinase. In a coupled reaction, catalyzed by glucose-6-phosphate dehydrogenase, NAD is reduced to NADH. The resulting absorbance change is proportional to the glucose concentration.

BUN/Creatinine

Plasma and dialysate samples were analyzed on a Boehringer Mannheim/Hitachi 704 Analyzer.

BUN: Urea is hydrolyzed by the action of urease. In a coupled reaction, NADH is oxidized to NAD. The resulting absorbance change is proportional to the concentration of urea.

Creatinine/Pap: Creatinine is converted to creatine by creatininase. Creatine is converted to sarcosine by creatinase. The oxidation of sarcosine by sarcosine oxidase produced hydrogen peroxide which is utilized in an indicator reaction in the formation of red benzoquinoneimine dye.

Results

The following calculations were performed based on sample analyses:

Net Ultrafiltration

Net ultrafiltration following an 8 hour dwell in all rats was determined as a difference between the infusion volume and the volume at the end of the 8 hour dialysis.

Peritoneal Volume

An estimate of dialysate volumes at 2 and 4 hours based on $^{14}$C dextran disappearance from dialysate during the dwell period. Intraperitoneal volume estimations at time t are based on the following equation:

$$Vt = \frac{DPM \text{ in} - \frac{[DPM \text{ in} - DPM \text{ out}] * t}{8}}{Ct/W}$$

Where:

DPM in=Volume infused*Concentration of $^{14}$C Dextran.
DPM out=Volume drained at 8 hrs*Concentration of $^{14}$C Dextran.
Ct=Concentration of $^{14}$C Dextran at time t.
W=body weight (kg).

Figure 2:
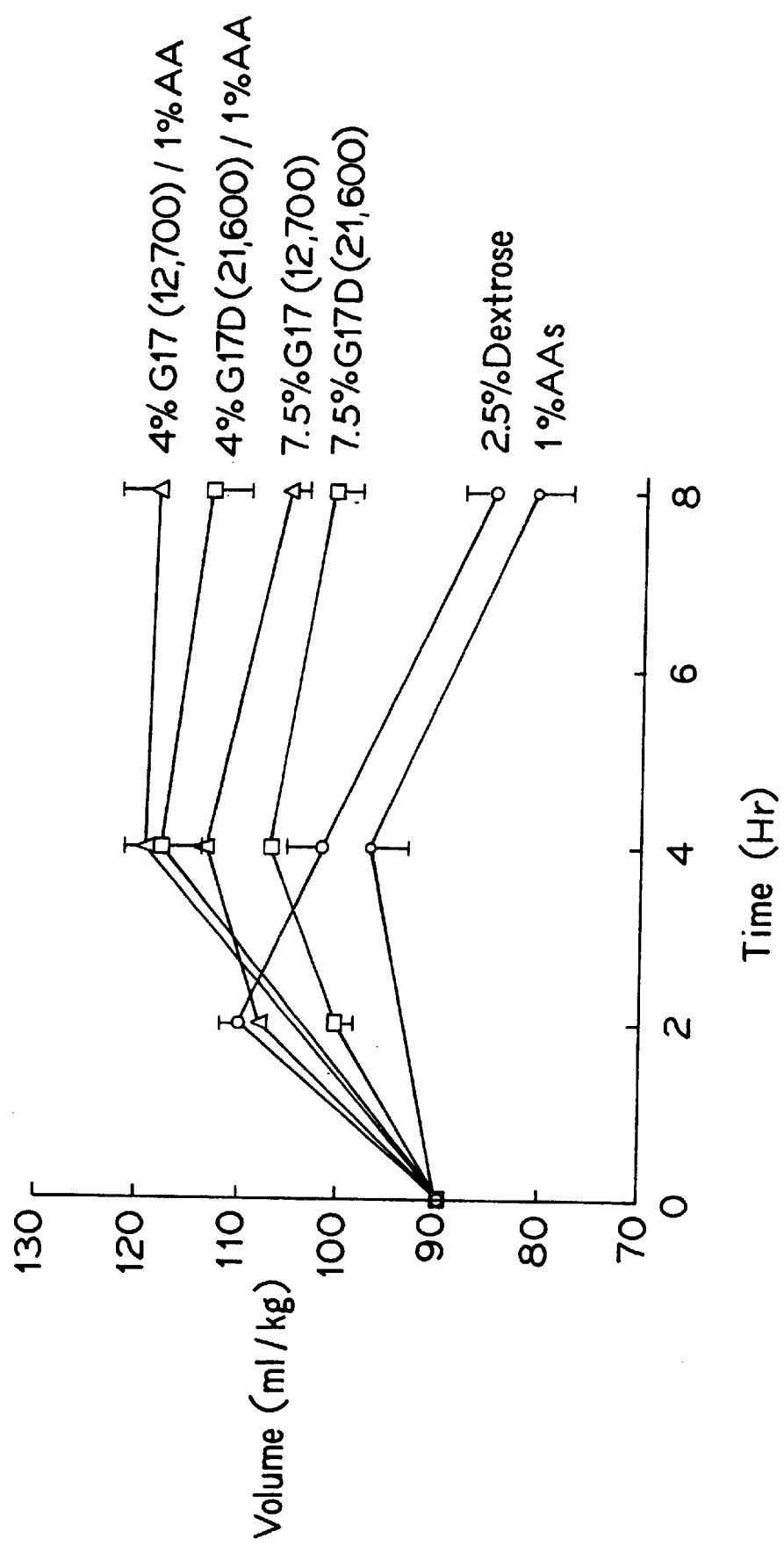
FIG. 2 illustrates graphically peritoneal volume profiles over time of solutions pursuant to the experiment set forth below.
Figure 3:
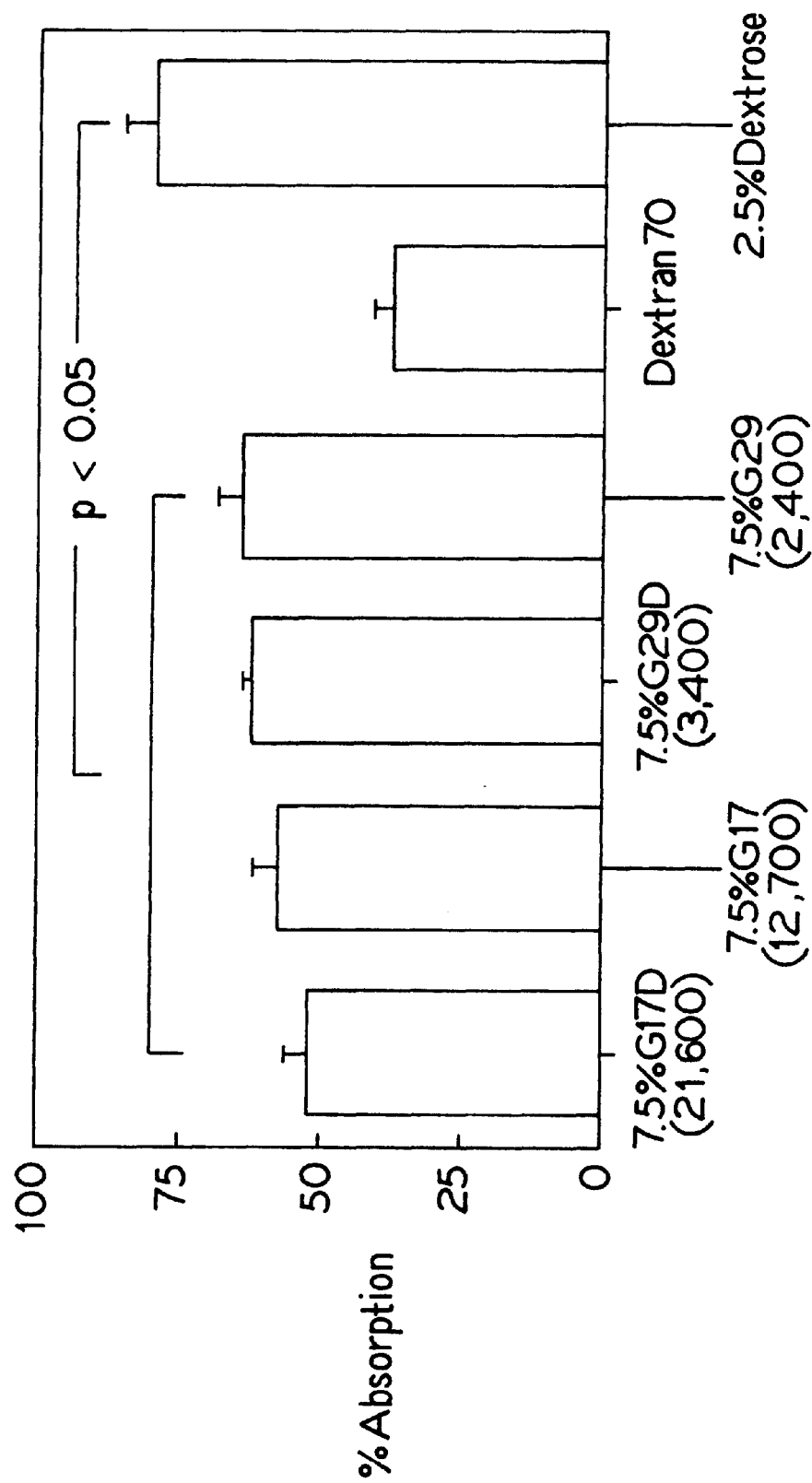
FIG. 3 illustrates graphically percent absorption of maltodextrins administered alone pursuant to the experiment set forth below.
Figure 4:
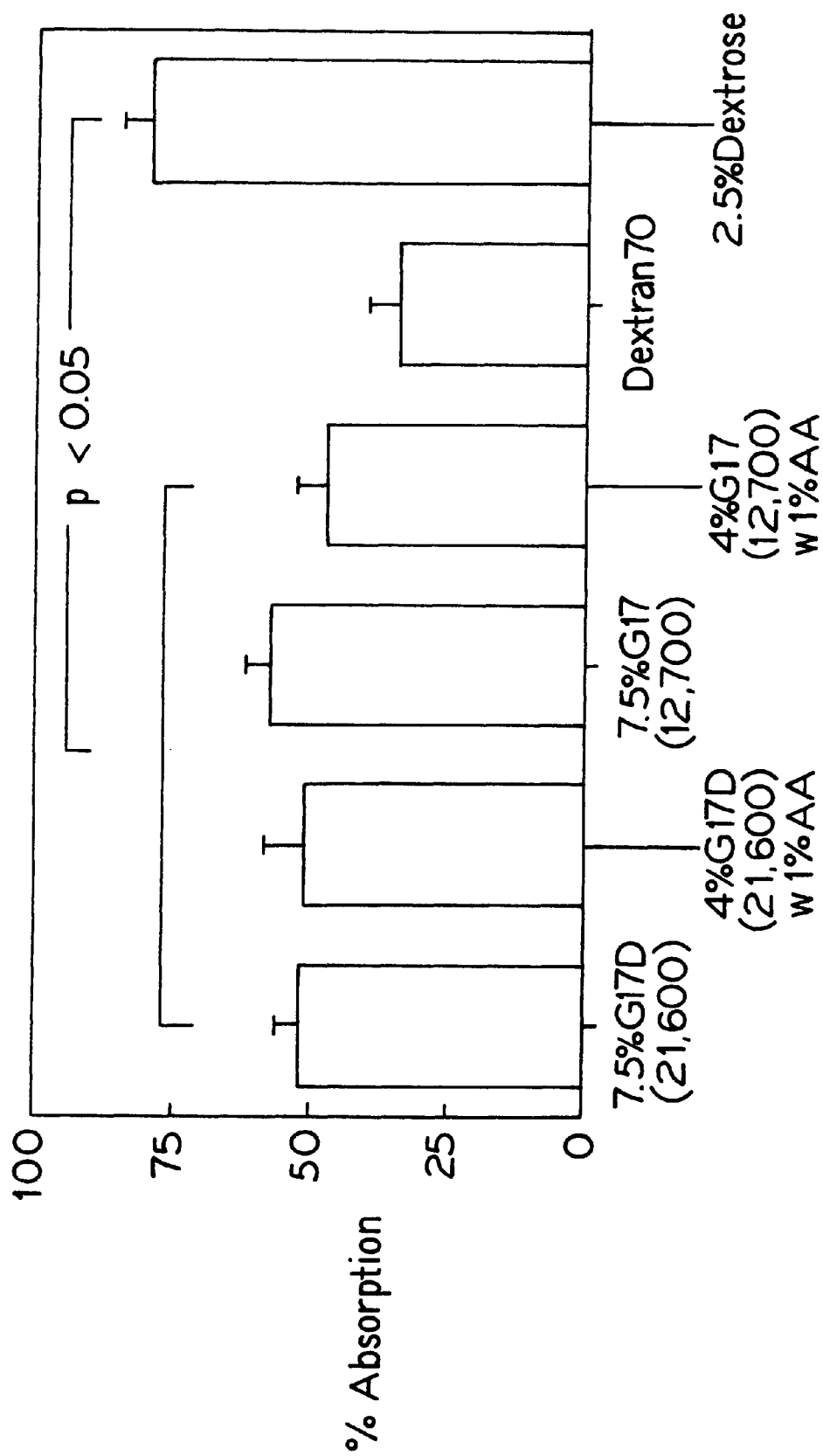
FIG. 4 illustrates graphically percent absorption for maltodextrins administered in combination with amino acids pursuant to the experiment set forth below.

Volume profiles are shown graphically in FIGS. 1 and 2. Volume profiles for 2.5% Dextrose Dianeal (n=11) from a previous study is included as a historic reference.

Dialysate Osmolality

Osmolality results at 2, 4, and 8 hours were determined.

Absorption of Osmotic Agents

Absorption (%) at each time interval was determined using the following equation:

$$\frac{[Vo * Co] - [Vt * Ct]}{[Vo * Co]} * 100$$

Where:

Vo=Volume infused (ml)
Co=Concentration (g/dl) of osmotic agent at t=0

Vt=Volume (ml) at time t
Ct=Concentration (g/dl) at time t
Note: Volumes at 2 and 4 hours were estimated based on $^{14}$C Dextran dilution.

The percent absorption of maltodextrins administered in combination was determined at 8 hours.

Results

Tukey's statistical analysis of the data generated in this study was performed. Mean group values were assessed for statistical significance at $\alpha=0.05$ as shown. Means under the same line are not significantly different.

| Parameter | Rank (High to Low) |
|---|---|
| Net UF | 6 4 5 3 2 1 7 |
| Absorption (8 hours) | 7 4 3 2 1 6 5 |
| Net UF/Gram Absorbed | 6 5 2 1 7 |

Where:
1=7.5% G17D
2=7.5% G17
3=7.5% G29D
4=7.5% G29
5=4% G17D+1% AA
6=4% G17+1% AA
7=2.5% Dextrose Dianeal Conclusions The FIGS. 1–5 illustrate graphically the results.

When administered alone, glucose polymers yield increased 8-hour drain volumes when compared to 2.5% Dianeal® in spite of lower initial osmolality. Addition of 1% amino acids allows a 46% reduction in the quantity of glucose polymers required to produce equivalent net UF at 8 hours.

The percent adsorption of glucose polymers is significantly lower than glucose alone at the end of 8 hours. The addition of amino acids does not change the percent of glucose polymer absorbed. Combination solutions (GP+ amino acids) provide higher net UF per g of osmotic agent absorbed.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A peritoneal dialysis solution comprising as an osmotic agent:

approximately 2.0 to about 6.0% (w/v) maltodextrins wherein the maltodextrins have the following characteristics:

| | |
|---|---|
| Weight Average Mol. Wt. (Mw) | 10,000–16,000 daltons |
| Number Average Mol. Wt. (Mn) | 4,000–8,000 daltons |
| Polydispersity | 1.0–4.0 |
| Fraction > 100,000 daltons | NMT 1.0% |
| Mono, Di, Trisaccharides | NMT 5.0% |
| Distribution | normal |
| Alpha (1–4) | NLT 90% |
| Aluminum (10% solution) | <10 ppb |
| Aqueous Solubility | NLT 10% (w/v) |
| pH (10% solution) | 5.0–7.0 |
| Heavy Metals | <5 ppm |
| DP (Degree of polymerization) greater than 20 | >75% |
| DP greater than 50 | >50% |
| DP greater than 100 | >25%; and | approximately 0.25 to about 2.0% (w/v) amino acids.

2. The peritoneal dialysis solution of claim 1 wherein the amino acids comprise both essential and non-essential amino acids.

3. The peritoneal dialysis solution of claim 1 further comprising sodium, chloride, lactate, bicarbonate, calcium, and magnesium.

4. The peritoneal dialysis solution of claim 1 wherein the solution further comprises:

120 to about 140 (mEq/L) sodium;

70 to about 110 (mEq/L) chloride;

0 to about 45.00 (mEq/L) of lactate;

0 to about 45.00 (mEq/L) of bicarbonate;

0 to about 4.00 (mEq/L) of calcium; and 0 to about 4.00 (mEq/L) of magnesium.

5. The peritoneal dialysis solution of claim 1 wherein the pH of the solution is approximately 6.0 to 7.4.

6. The peritoneal dialysis solution of claim 1 wherein the maltodextrins have the following characteristics:

| | |
|---|---|
| Weight Average Mol. Wt. (Mw) | 10,000–16,000 daltons |
| Number Average Mol. Wt. (Mn) | 4,000–8,000 daltons |
| Polydispersity | 1.0–4.0 |
| Fraction > 100,000 daltons | NMT 1.0% |
| Mono, Di, Trisaccharides | NMT 5.0% |
| Distribution | normal |
| Alpha (1–4) | NLT 90% |
| Aluminum (10% solution) | <10 ppb |
| Aqueous Solubility | NLT 10% (w/v) |
| pH (10% solution) | 5.0–7.0 |
| Heavy Metals | <5 ppm |
| DP (Degree of polymerization) | |
| greater than 20 | ≧75% |
| DP greater than 50 | ≧50% |
| DP greater than 100 | ≧25%. |

7. The peritoneal dialysis solution of claim 1 wherein the maltodextrins are derived from the hydrolysis of starch.

8. A peritoneal dialysis solution comprising as an osmotic agent: approximately 2.0 to about 6.0% (w/v) maltodextrins and approximately 0.25 to about 2.0% (w/v) amino acids, the amino acids comprise:

| Amino Acid | Conc. (mg %) |
|---|---|
| Leucine | 74–112 |
| Valine | 100–151 |

-continued

| Amino Acid | Conc. (mg %) |
|---|---|
| Threonine | 47–71 |
| Isoleucine | 61–92 |
| Lysine.HCl | 55–83 |
| Histidine | 52–78 |
| Methionine | 32–48 |
| Phenylalanine | 42–62 |
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83. |

9. The peritoneal dialysis solution of claim 1 wherein the amino acids are chosen so as to have the following ratios:
Phenylalanine/Tyrosine 1.3–3.0
Essential/Total Amino Acids 0.4–0.7.

10. The peritoneal dialysis solution of claim 1 wherein maltodextrins and amino acids comprise the only components of the osmotic agent.

11. A peritoneal dialysis solution comprising:

| | |
|---|---|
| Maltodextrins (% w/v) | 2.0–6.0 |
| Amino Acids (% w/v) | 0.25–2.0 |
| Sodium (mEq/L) | 120–140 |
| Chloride (mEq/L) | 70–110 |
| Lactate (mEq/L) | 0.0–45.0 |
| Bicarbonate (mEq/L) | 0.0–45.0 |
| Calcium (mEq/L) | 0.0–4.0 |
| Magnesium (mEq/L) | 0.0–4.0 |
| pH | 6.0–7.4; and | the maltodextrins being characterized in that the maltodextrins have a DP (Degree of polymerization) so that:

| | |
|---|---|
| DP greater than 20 | ≧75% |
| DP greater than 40 | ≧50% |
| DP greater than 80 | ≧25%. |

12. The peritoneal dialysis solution of claim 11 wherein the maltodextrins are derived from the hydrolysis of starch and have the following composition:

| | |
|---|---|
| Weight Average Mol. Wt. (Mw) | 10,000–16,000 daltons |
| Number Average Mol. Wt. (Mn) | 4,000–8,000 daltons |
| Polydispersity | 1.0–4.0 |
| Fraction > 100,000 daltons | NMT 1.0% |
| Mono, Di, Trisaccharides | NMT 5.0% |
| Distribution | normal |
| Alpha (1–4) | NLT 90% |
| Aluminum (10% solution) | <10 ppb |
| Aqueous Solubility | NLT 10% (w/v) |
| pH (10% solution) | 5.0–7.0 |
| Heavy Metals | <5 ppm |
| DP (Degree of polymerization) | |
| greater than 20 | ≧75% |
| DP greater than 40 | ≧50% |
| DP greater than 80 | ≧25%. |

13. The peritoneal dialysis solution of claim 11 wherein the amino acids comprise:

| Amino Acid | Conc. (mg %) |
|---|---|
| Leucine | 74–112 |
| Valine | 100–151 |
| Threonine | 47–71 |
| Isoleucine | 61–92 |
| Lysine.HCl | 55–83 |
| Histidine | 52–78 |
| Methionine | 32–48 |
| Phenylalanine | 42–62 |
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83. |

14. The peritoneal dialysis solution of claim 11 wherein the amino acids are chosen so as to have the following ratios:

| | |
|---|---|
| Phenylalanine/Tyrosine | 1.3–3.0 |
| Essential/Total Amino Acids | 0.4–0.7. |

15. The peritoneal dialysis solution of claim 11 wherein maltodextrins and amino acids comprise the only components of the osmotic agent.

16. A method for providing an osmotic agent for use in a peritoneal dialysis solution comprising the steps of:
selecting as a first component of the osmotic agent a first composition having a molecular weight equal to or greater than 10,000 daltons and comprising approximately 2.0 to about 6.0% (w/v) of the dialysis solution; and
selecting as a second component of the osmotic agent a second composition having a molecular weight equal to or less than 300 daltons and comprising approximately 0.25 to about 2.0% w/v of the dialysis solution.

17. The method of claim 16 wherein the osmotic agent includes maltodextrin and amino acids.

18. The method of claim 17 wherein the maltodextrins are derived from the hydrolysis of starch and have the following composition:

| | |
|---|---|
| Weight Average Mol. Wt. (Mw) | 10,000–16,000 daltons |
| Number Average Mol. Wt. (Mn) | 4,000–8,000 daltons |
| Polydispersity | 1.0–4.0 |
| Fraction > 100,000 daltons | NMT 1.0% |
| Mono, Di, Trisaccharides | NMT 5.0% |
| Distribution | normal |
| Alpha (1–4) | NLT 90% |
| Aluminum (10% solution) | <10 ppb |
| Aqueous Solubility | NLT 10% (w/v) |
| pH (10% solution) | 5.0–7.0 |
| Heavy Metals | <5 ppm |
| DP (Degree of polymerization) | |
| greater than 20 | ≧75% |
| DP greater than 50 | ≧50% |
| DP greater than 100 | ≧25%. |

19. The method of claim 17 wherein the amino acids comprise:

| Amino Acid | Conc. (mg %) |
|---|---|
| Leucine | 74–112 |
| Valine | 100–151 |
| Threonine | 47–71 |
| Isoleucine | 61–92 |
| Lysine.HCl | 55–83 |
| Histidine | 52–78 |
| Methionine | 32–48 |
| Phenylalanine | 42–62 |
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83. |

20. A two part peritoneal dialysis solution designed to be mixed prior to infusion into a patient comprising:

a first part housed in a first structure including approximately 2.0 to about 6.0% (w/v) maltodextrin and a pH of approximately 4.0 to about 5.5;

a second part housed in a second structure including amino acids; and including in either the first or the second structure a sufficient amount of the following ingredients so when the first part and second part are mixed the following is provided: 120 to about 140 (mEq/L) sodium; 70.0 to about 110.00 (mEq/L) chloride; 0.0 to about 5.0 (mEq/L) lactate; 0.0 to about 45.0 (mEq/L) bicarbonate; 0.0 to about 4.0 mEq/L) calcium; and 0.0 to about 4.0 (mEq/L) magnesium.

21. The two part peritoneal dialysis solution of claim 20 wherein the first and second structures are two separate chambers of a single container.

22. The two part peritoneal dialysis solution of claim 20 wherein the pH of a resultant solution, comprising a mixture of the first part and the second part, is approximately 6.0 to about 7.4.

* * * * *

UNITED STATES PATENT AND TRADEMARK OFFICE
CERTIFICATE OF CORRECTION

PATENT NO. : 6,306,836 B1
DATED : October 23, 2001
INVENTOR(S) : Leo Martis et al.

It is certified that error appears in the above-identified patent and that said Letters Patent is hereby corrected as shown below:

Column 7,
Line 34, delete "With" and insert -- with --

Column 8,
Line 43, delete "06" and insert -- 96 --

Column 13,
Line 63, delete "40" and insert -- 50 --
Line 64, delete "80" and insert -- 100 --

Signed and Sealed this

Seventh Day of May, 2002

Attest:

JAMES E. ROGAN
Attesting Officer     *Director of the United States Patent and Trademark Office*